United States Patent
Carroll et al.

[11] Patent Number: 5,421,207
[45] Date of Patent: Jun. 6, 1995

[54] ALIGNMENT COUPLING FOR FIXED ALIGNMENT AND FREE SWIVELING ACTION

[76] Inventors: Norman L. Carroll, 156 Merritt Dr., Butler, Pa. 15007; Willard L. Pearce, 2315 Big Rock, Allison Park, Pa. 15101

[21] Appl. No.: 114,454

[22] Filed: Sep. 1, 1993

[51] Int. Cl.⁶ .................................................. G01N 3/04
[52] U.S. Cl. ............................................................. 73/856
[58] Field of Search ........................ 73/856, 849, 826; 333/712, 787, 790; 24/68 C, 68 D, 514, 525

[56] References Cited

U.S. PATENT DOCUMENTS

| | | | |
|---|---|---|---|
| 2,454,850 | 11/1948 | Van Winkle et al. | 73/856 |
| 3,005,336 | 10/1961 | Wyman | 73/860 |
| 3,107,524 | 10/1963 | O'Connor | 73/860 |
| 3,631,604 | 1/1972 | Schenavar | 33/572 |
| 3,881,694 | 5/1975 | Gardner | 24/68 D X |
| 3,922,906 | 12/1975 | Snitko et al. | 73/65.01 X |
| 3,938,373 | 2/1976 | Fletcher et al. | 73/833 |
| 4,102,018 | 7/1978 | Kawahara | 24/68 D X |
| 4,398,350 | 8/1983 | Inoue | 33/644 |
| 4,686,860 | 8/1987 | Liu | 73/856 |
| 4,721,000 | 1/1988 | Scanlon | 73/833 |
| 4,843,888 | 7/1989 | Gram et al. | 73/856 |
| 4,845,997 | 7/1989 | Radin et al. | 73/831 |
| 4,888,995 | 12/1989 | Curtis | 73/859 |
| 5,138,887 | 8/1992 | Pohl | 73/856 |

FOREIGN PATENT DOCUMENTS

| | | | |
|---|---|---|---|
| 3731460 | 4/1988 | Germany. | |
| 61-277032 | 12/1986 | Japan | 73/826 |

*Primary Examiner*—Richard E. Chilcot, Jr.
*Assistant Examiner*—James M. Olsen
*Attorney, Agent, or Firm*—Daniel W. Ernsberger

[57] ABSTRACT

An alignment coupling is shown which is of chain like construction where one pair of set screws passes through the upper link and engages the top of the lower link so as to adjust its alignment and a second pair of set screws passes through the lower link and engages the bottom of the upper link to adjust its alignment. This coupling is used in a free swiveling mode or a fixed alignment mode.

1 Claim, 1 Drawing Sheet

ALIGNMENT COUPLING FOR FIXED ALIGNMENT AND FREE SWIVELING ACTION

BACKGROUND OF THE INVENTION

Alignment couplings are useful parts of materials testing apparatus. Free swiveling alignment couplings are used above and below a sample to relieve the bending strain on the sample. Double knife edge couplings are commonly used for this purpose. Fixed alignment couplings are used to change the alignment of the load train and keep it in a fixed position.

Alignment fixtures and free moving alignment couplings do not eliminate bending strains. The present invention can be used to reduce the bending strain and, if desired, to subject to the sample to a known bending strain.

SUMMARY OF THE PRESENT INVENTION

The novel coupling of the present invention permits both free swiveling motion and fixed alignment. In the most preferred embodiment of the invention, a double knife edge coupling is modified by introduction of four set screws which permit free swiveling motion when they are loosened, change the angular alignment of the coupling as the screws are tightened and fix the angular alignment of the coupling when all are tightened.

GENERAL DESCRIPTION OF THE DRAWINGS

DETAILED DESCRIPTION OF THE INVENTION

Figure 1:
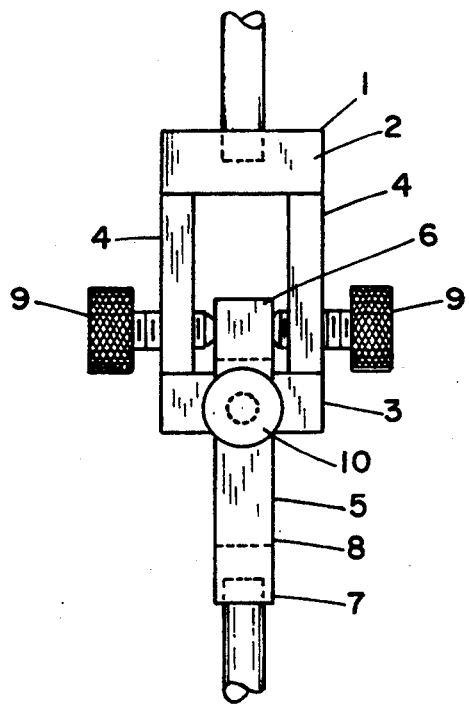
FIG. 1 and 2 are front and side views of a modified chain coupling.
Figure 2:
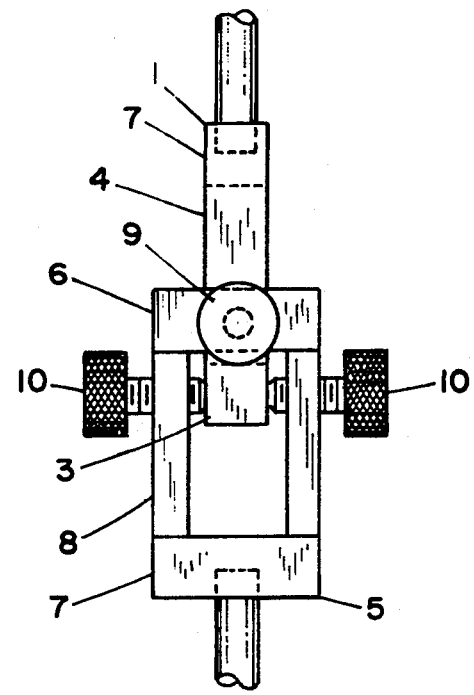

The alignment coupling is generally shown in FIGS. 1 and 2. It is chain like in construction comprising an upper link, 1, having a head, 2, a foot 3 and two sides, 4 and a lower link, 5 having a head, 6 a foot, 7 and two sides, 8. Two set screws, 9 are threadedly engaged to the opposing sides of the upper link, 1. Each screw is adapted to engage the head of the lower link, 5. Two more set screws, 10 are threadedly engaged to the opposing sides of the lower link, 5. Again each screw is adapted to engage the foot of the upper link, 1.

Figure 3:
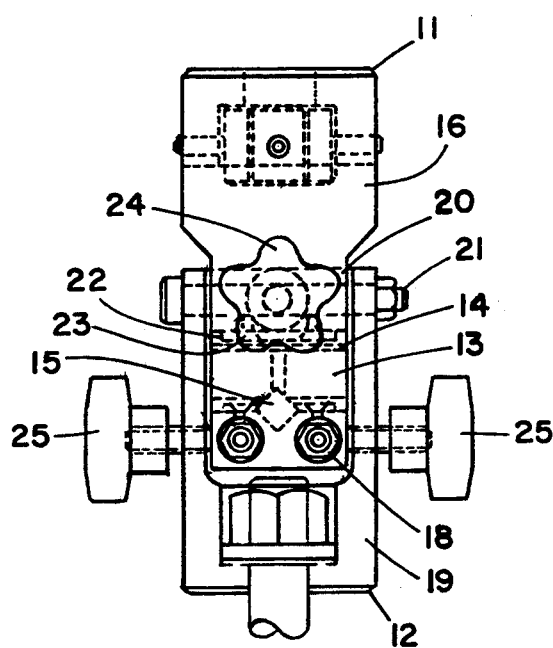
FIG. 3 and 4 is front view and side view of the modified double knife edge alignment coupling.
Figure 4:
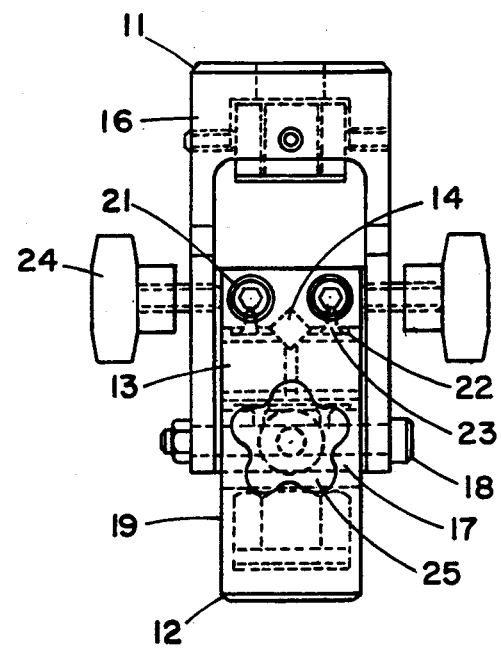

While the contact between the upper link and the lower link can be of many possible configurations, the preferred configuration is a double knife edge. FIGS. 3 and 4 show a front view and side view of the modified double knife edge alignment coupling. This is the preferred design for the chain coupling described above. The coupling is chainlike in construction with an upper link, 11 and a lower link, 12, separated by a floating v-block, 13 that is compressed between an upper knife edge, 14 and a lower knife edge, 15. The upper link consists of a buttonhead clevis, 16, closed with a shoulder block, 17, and secured with two shoulder bolts, 18. The lower link is a threaded clevis, 19, closed with a shoulder block 20 and secured with two shoulder bolts, 21. (The knife edges, 14 and 15, are secured to their shoulder blocks, 17 and 20, with brackets, 22 and screws, 23.) This double knife edge alignment fixture is modified to permit fixed alignment by the introduction of two pairs of knobbed set screws, 24 and 25. One pair of opposing set screws, 24 pass through the sides of the button head clevis, 16, and, when one is advanced, and the other withdrawn, the advancing screw applies pressure on a shoulder block, 20, and causes the threaded clevis, 19 to rotate on its knife edge, 14. Similarly, the second pair of opposing set screws, 25, pass through the sides of the threaded clevis, 19, and, when one is advanced, and the other withdrawn the advancing screw applies pressure on a shoulder block, 17 and causes the button head clevis, 16 to rotate on its knife edge, 15. The alignment coupling becomes fixed when both pairs of set screws are advanced and tightened against their shoulder blocks.

We claim:
1. An alignment coupling comprising
   an upper link having a head a foot and two sides and
   a lower link having a head a foot and two sides and
   two set screws threadedly engaged to the opposing sides of the upper link, each screw adapted to engage the head of the lower link and
   two set screws threadedly engaged to the opposing sides of the lower link, each screw adapted to engage the foot of the upper link, and
   the Upper link and lower link being separated by a floating v-block that is compressed between a knife edge fixedly attached to the lower link and a knife edge fixedly attached to the upper link.

* * * * *